United States Patent
Gantefort

(10) Patent No.: US 8,283,159 B2
(45) Date of Patent: Oct. 9, 2012

(54) FERMENTER FOR PRODUCING BIOGAS FROM ORGANIC MATERIAL

(75) Inventor: Wilhelm Gantefort, Heiden (DE)

(73) Assignees: Wilheim Gantefort, Heiden (DE); Jurgen Beck, Rottenburg (DE)

( * ) Notice: Subject to any disclaimer, the term of this patent is extended or adjusted under 35 U.S.C. 154(b) by 856 days.

(21) Appl. No.: 12/093,062

(22) PCT Filed: Oct. 20, 2006

(86) PCT No.: PCT/EP2006/010127
§ 371 (c)(1), (2), (4) Date: Sep. 8, 2008

(87) PCT Pub. No.: WO2007/054193
PCT Pub. Date: May 18, 2007

(65) Prior Publication Data
US 2009/0305376 A1    Dec. 10, 2009

(30) Foreign Application Priority Data
Nov. 11, 2005  (DE) .................. 10 2005 054 323

(51) Int. Cl.
C12M 1/107 (2006.01)
C12M 3/00 (2006.01)

(52) U.S. Cl. ............... 435/300.1; 435/292.1; 435/289.1; 435/297.1; 435/297.2; 435/299.1; 435/304.1; 210/603; 48/197 R; 48/198.6; 48/197 A

(58) Field of Classification Search ............... 435/300.1, 435/295.1, 292.1, 289.1, 297.1, 297.2, 299.1, 435/304.1; 210/603; 48/197 R, 197 A, 198.6
See application file for complete search history.

(56) References Cited

U.S. PATENT DOCUMENTS

| | | | | |
|---|---|---|---|---|
| 3,853,752 A * | 12/1974 | Tymoszczuk | | 210/618 |
| 6,391,628 B1 * | 5/2002 | Lipp | | 435/295.1 |
| 6,548,027 B1 * | 4/2003 | Hall et al. | | 422/186.04 |
| 6,660,518 B1 * | 12/2003 | Maekawa | | 435/291.1 |
| 7,008,538 B2 * | 3/2006 | Kasparian et al. | | 210/610 |
| 8,093,041 B1 * | 1/2012 | Nirmalakhandan et al. | | 435/292.1 |

FOREIGN PATENT DOCUMENTS

| | | |
|---|---|---|
| DE | 3100324 A1 | 8/1982 |
| DE | 3604415 A1 | 8/1987 |
| DE | 19538579 C1 | 4/1997 |

(Continued)

OTHER PUBLICATIONS

Machine Translation of DE 10127228, completed Jan. 2011.*

(Continued)

Primary Examiner — William H Beisner
Assistant Examiner — Danielle Henkel
(74) Attorney, Agent, or Firm — Rankin, Hill & Clark LLP

(57) ABSTRACT

The invention relates to a fermenter (10) for producing biogas from organic material, having a fermentation chamber (11) with a substantially round basal surface to receive fermentation material; arranged, in the peripheral region of the fermentation chamber, filling means (12) for substrate to be fermented; arranged, above the fermentation chamber, an unpressurized gas store (13) with gas discharging means (14); stirring means (15); a settling chamber (16) with overflow rim; and also pumping means (17) for the continuous or batchwise removal of fermentation material from the fermentation chamber and introduction into the settling chamber.

27 Claims, 4 Drawing Sheets

FOREIGN PATENT DOCUMENTS

| | | |
|---|---|---|
| DE | 197 46 636 A1 | 4/1999 |
| DE | 19756485 A1 | 7/1999 |
| DE | 10127228 * | 3/2005 |
| DE | 10347476 A1 | 4/2005 |
| EP | 0 335 825 A1 | 10/1989 |
| EP | 0 521 302 A2 | 1/1993 |
| WO | 84/00038 | 1/1984 |

OTHER PUBLICATIONS

Nordenskjoeld Reinhart Von, Methane gas generator provided with cavity wall strucutre, DE19746636 (1999) EPO Machine Translation retrieved Feb. 2012.*

* cited by examiner

FERMENTER FOR PRODUCING BIOGAS FROM ORGANIC MATERIAL

The present invention relates to a fermenter for producing biogas from organic material.

Interest in fermenters for producing biogas has increased since there has been increased public discussion about renewable energy sources and how to encourage their use. These fermenters are known from use in agriculture, and also in municipal sewage-treatment plants. A principle of these fermenters is that organic material is stored in a closed container, and the organic carbon compounds present are degraded via microbial activity to give methane gas, which is collected and used for producing heat and/or electrical power. The energy thus obtained is almost $CO_2$-neutral, since the carbon dioxide released during the combustion process has previously been removed from the atmosphere by photosynthesis of plants.

Whereas in the past it was almost exclusively organic waste that was used for producing biogas, examples being sewage sludge, animal excrement from agriculture, or wood-chip waste, in more recent times primary agricultural products have increasingly been used for producing biogas, since these have a much higher proportion of organically bound carbon and thus are considered likely to give a higher yield of methane gas. The increasing level of interest in renewable energy sources has therefore increasingly led to a focus on these methods of production.

The fermentation process for producing biogas, which proceeds with exclusion of oxygen, will first be described below.

The overall fermentation process can be divided into a number of phases. In the first phase, the carbohydrates, fats, and proteins present in the substrate for fermentation are converted into low-molecular-weight hydrocarbon compounds ($C_1$-$C_5$ units) via microorganisms which are facultative and obligate anaerobes. Carbohydrates are successively degraded here to give propionic acid or butyric acid and, respectively, butanol, and fatty acids are decomposed by the β-oxidation route stepwise to give $C_2$ units, which are released in the form of acetic acid, and amino acids are degraded by a coupled mechanism in the Stickland reaction to give acetic acid, ammonia, and $CO_2$.

These intermediates are in turn degraded to give the methanogenic substrates acetic acid ($CH_3COOH$), hydrogen ($H_2$), carbonic acid ($H_2CO_3$), formic acid (HCOOH), and methanol ($CH_3OH$).

These methanogenic substrates are in turn degraded by methane-forming (methanogenic) bacteria of the genera *Methanobacterium*, *Methanosarcina*, and *Methanospirillum* which are obligate anaerobes, to give methane, carbon dioxide, and water in the following reactions:

$$CH_3COO^- + H^+ \rightarrow CH_4 + CO_2 \quad 1)$$

$$HCO_3^- + H^+ + 4H_2 \rightarrow CH_4 + 3H_2O \quad 2)$$

$$HCOO^- + H^+ + 3H_2 \rightarrow CH_4 + 2H_2O \quad 3)$$

$$CH_3OH + H_2 \rightarrow CH_4 + H_2O \quad 4)$$

More than 70% of the methane is produced by way of the cleavage of acetic acid, i.e. by way of reaction 1.

Since methane gas fermentation is a mixed process in which various microorganisms are active in the various phases, the different demands of all of the microorganisms have to be taken into account in order to maximize yield. However, the conditions required for the activity of the methanogenic bacteria are decisive.

The latter need a strictly oxygen-free environment, because of their properties as obligate anaerobes. They moreover prefer a slightly alkaline pH.

A fact which is important in this context is that biological systems subject to anoxic conditions in principle tend toward acidification. This is because many microorganisms switch to glycolytic energy generation in the absence of oxygen, thus producing large amounts of acidic metabolites, e.g. lactate, which contribute to acidification of the environment. In methane gas fermentation, too, the first and second phase produce acidic metabolites (acetic acid, formic acid), which lead to a lowering of the pH.

In contrast, slurry is an anoxic system with relatively high pH. This makes slurry highly suitable for creating the conditions required for methane bacteria in a biogas fermenter.

The solids content should not be excessively low, since solids serve as an area of colonization and contact for the methanogenic bacteria, but should also not be excessively high. A solids content in the range from 2 to 9% has been found to be suitable.

The temperature should be in the range from 30° C. to 60° C. In many instances, a biogas fermenter therefore requires temperature control. Heating equipment, for example heat exchangers arranged in the fermenter, often have a relatively high temperature at their surface. Fermentation material which comes into contact with the heating equipment is therefore heated initially to a temperature above the preferred temperature range, and then passes this temperature on successively to the surrounding material. Although this method permits establishment of the desired temperature in the overall fermentation chamber, the elevated temperature in the region of the heating equipment kills the methanogenic bacteria that have colonized that region, and therefore reduces yield.

Good mixing has to be provided, for uniform supply of nutrients and ideal utilization of space, and in order to avoid any increase in the concentration of toxic intermediates. This can also inhibit formation of surface scum, which is composed of fats and of free fatty acids, and firstly inhibits degassing and secondly is not an available substrate for methanogenesis.

DE 197 564 85 discloses a septic tank with agitator for use in agricultural biogas plants and in municipal sewage-treatment plants. This has a round floor area, a feed neck, and, attached at the periphery of the septic tank, an agitator with a drive axis. The agitator is accommodated in an agitator tube arranged underneath the feed neck. The agitator tube preferably runs vertically. The contents of the fermentation container are temperature-controlled by way of wall heating. Substrate to be fermented is introduced into the fermentation container by way of a feed neck arranged relatively close to the top, while exhausted fermented material located further down within the container is pumped away by way of a discharge system arranged very much further down, and is passed to fermentation-residue storage.

For various reasons, the septic tank described does not provide ideal conditions for methanogenic bacteria to thrive. For example, formation of surface scum is not reliably prevented. The arrangement of a heating system in the region of the wall moreover leads to undesired temperature gradients, which as mentioned above lead to a reduction of the activity of the bacteria in the region of the wall. The same applies, incidentally, to heat exchangers or heating systems arranged in the interior of a fermentation chamber.

The material removed via the discharge system and passed to fermentation residue storage has not moreover completely finished fermenting. Since fermentation residue storage does not generally provide controlled conditions or have any apparatus for gas collection, a portion of the possible yield is lost here.

It is an object of the present invention to provide a fermenter which can produce biogas from organic material and which has higher yields when compared with apparatuses of the prior art.

A further object of the present invention is to provide a process which can produce biogas from organic material and which is considered likely to have higher yields than processes known from the prior art.

The present invention provides a fermenter for producing biogas from organic material having a fermentation chamber with a essentially round base surface to receive fermentation material, and, arranged in the peripheral region of the fermentation chamber, filling means for substrate to be fermented, and, arranged above the fermentation chamber, an unpressurized gas store with gas discharging means, and also agitation equipment.

The fermenter also has a settling chamber with overflow rim, and also pumping means for the continuous or batchwise removal of fermentation material from the fermentation chamber and introduction into the settling chamber.

The design of the settling chamber is such that the fermentation material introduced from the fermentation chamber settles and the active biomass, i.e. living microorganisms, in particular methane bacteria, and also substrates to be metabolized, in particular methanogenic substrates, can rise, while the substantially exhausted fermentation material (passive biomass) sinks.

As described at a later stage below, this clearly provides a way of reclaiming the active biomass and reintroducing it to the fermentation process, whereas in apparatuses of the prior art it is passed together with the finished fermentation material to fermentation-residue storage, where it has no further use. This substantially increases the yield.

In addition to this, the return of the active biomass to the fermentation chamber substantially shortens the period for optimization of the plant on start-up. A biogas plant in principle requires a certain time for optimization. The reason for this is that a stable microorganism flora must first become established in the plant. The possibility of reclaiming the microorganisms remaining in the fermented material removed from the fermentation chamber considerably shortens the period required to build a stable microflora. The time needed to reach maximum yield is thus substantially shorter.

The possibility of return of the active biomass has a further advantage: the fermentation process is accelerated, since the density of colonization by active microorganisms in the fermentation chamber can be maintained at a substantially higher level. The throughput of the fermenter can therefore be increased. An inventive fermenter can therefore tolerate substantially higher loading per unit of volume.

Any marked excess over an OS (organic solids) loading of about 1.5 to 2.0 kg $m^{-3}$ $d^{-1}$ in the fermentation chamber is generally considered inadvisable, since higher loading per unit of volume reduces yield. However, much higher loading per unit of volume is possible with the aid of the measures mentioned in the inventive fermenter. The inventive fermenter therefore firstly has a better yield per ton of material used, and secondly also permits higher throughput per unit of time. These two factors make a substantial contribution to considerably improved cost-effectiveness of the inventive fermenter.

It is preferable here firstly that the fermentation material is removed in the lower region of the fermentation chamber. This procedure provides a reduction in the content of active biomass in the fermentation material removed from the fermentation chamber.

It is secondly preferable that the fermentation material is not introduced into the settling chamber from above, but instead in a region below the overflow rim. When the fermentation material is introduced into the settling chamber, the active biomass that has settled in its upper region is thus displaced upward and runs over the overflow rim, and can therefore be reintroduced into the fermentation process in the fermentation chamber.

In another preferred embodiment of the inventive apparatus, the fermentation chamber has been designed in the form of an annular channel.

The technical management of a fermentation chamber designed in this way is easy. Appropriate agitators can be used to establish an easily controllable circumferential flow of material, and it is easy to control the occurrence of sediment layers and scum layers.

In one particularly preferred embodiment, the settling chamber has, in its lower region, a fixed-bed reactor composed of solid material.

This solid material can, for example, be porous material, e.g. a bed composed of lava granules or of swellable clay particles. A plastics matrix, for example composed of plastics granules, is likewise suitable. A factor important for this fixed-bed reactor is that it firstly has downward permeability and secondly has a large internal surface area, thus permitting colonization by a maximum number of microorganisms.

The fixed-bed reactor successively accepts the exhausted fermentation material introduced from above and brings it into close contact with its inner surface densely colonized by microorganisms. At the same time, the throughput of material is markedly slowed. This procedure can also ferment residues of organic carbon compounds remaining in the material, and the yield of the inventive fermenter is further improved.

Below the fixed-bed reactor there is preferably pumping means for the removal of residual exhausted fermented material. This can be put in fermentation-residue storage, has been completely exhausted by the fermentation process, and therefore comprises practically no remaining organic constituents. Its structure is moreover substantially more homogeneous than that of conventional fermentation residues, and its properties are more uniform and more consistent. It is moreover less contaminated by scum and sediment. It can therefore in particular be used as fertilizer.

In one particularly preferred embodiment, the volume of the fermentation material introduced into the settling chamber is greater than the volume of the residual material removed from the fixed-bed reactor.

On introduction of the fermentation material into the settling chamber, the active biomass which has risen to the top in the chamber is thus displaced upward and runs over the overflow rim, and can therefore be reintroduced into the fermentation process in the fermentation chamber.

A conical design of the surface of the fixed-bed reactor can be used to achieve a further improvement in the discharge of the active biomass into the fermentation chamber.

It is moreover particularly preferable that the settling chamber has been arranged in the center of the fermentation chamber, and equally in the center of the fermentation chamber designed in the form of an annular channel. This design has many advantages in terms of heat management, apparatus technology, and process technology. However, if desired or if necessary, the settling chamber can also have been arranged outside of the fermentation chamber.

The stirring means has preferably been arranged in the peripheral region of the fermentation chamber. This arrangement permits easy production of a circumferential flow of material and high efficiency of mixing. The direction of conveying can be reversed at intervals which may be relatively regular or relatively irregular, for example once daily, in order to prevent blockages in the system and to bring about resuspension of deposits.

Because their density is relatively low, the above-mentioned intermediates and methanogenic substrates tend in principle to rise within the fermentation mass and form a scum layer. These substances thus become unavailable to the metabolism of the microorganisms mentioned, in particular methane bacteria, the result being reduced yield of the fermenter.

In one particularly preferred embodiment of the inventive apparatus, the stirring means is therefore designed in such a way that it sucks material from the surface of the fermentation mass and forces it obliquely downward, and specifically in such a way that a sigmoid flow of material can be produced in the region of the agitation equipment. Production of a scum layer is thus prevented, and the intermediates and methanogenic substrates are conveyed back into the fermentation mass, and fed to the microorganisms.

This measure substantially increases the yield of the fermenter. This measure also contributes to faster achievement of the ideal conditions in the fermenter, and permits higher OS load per unit of volume—with the abovementioned advantages.

Furthermore, this also permits effective fermentation of substrates which have a marked tendency to form scum layers and which are difficult to use in conventional fermenters. Interestingly, these substrates are specifically very high-energy-content substrates which potentially promise a very high methane yield, examples being high-fat-content substrates, such as rapeseed cake, waste fat, floatation fat, or bakery waste. The biogas-formation potential of these substrates is from $400 \text{ m}^3 \text{ t}^{-1}$ to $650 \text{ m}^3 \text{ t}^{-1}$, and they are therefore some of the most desirable substrates.

Although these substrates are waste materials, some of them are relatively expensive. For example, rapeseed cake is also in demand for animal feed. The arrangement described is the first to permit effective fermentation of the substrates and thus make full use of their overall biogas-formation potential, and is thus—in view of the high price of these materials—the first to permit their cost-effective use as substrate in a biogas plant.

The stirring means is preferably composed of two agitators. Each of these has, for example, drive equipment, a shaft, and a propeller with blades, and each preferably has variable rotation rate and is adjustable in relation to its angle, i.e. for example the angle of the shaft, in relation to the horizontal axis and/or to the vertical axis.

It is possible here that the direction of orientation of one of the two agitators is obliquely upward and that of the other is obliquely downward, and the direction of orientation of each of the two agitators here passes different sides of the vertical central axis of the fermentation chamber.

With the aid of this arrangement it is easy to establish the sigmoid and otherwise circumferential flow of material mentioned, in the region of the agitation equipment.

To improve control of the flow of material, there can moreover be baffles in the peripheral region of the fermentation chamber.

The stirring means can also be composed of a channel running obliquely on the inner side of the outer wall of the fermentation chamber, with only one agitator. This channel is also capable of establishing a sigmoid and otherwise circumferential flow of material in the region of the agitation equipment.

In one particularly preferred embodiment of the inventive fermenter, the fermenter has temperature-control equipment set up in such a way that the temperature of the fermentation material in the fermentation chamber can be adjusted solely via the temperature control of the substrate intended for fermentation and introduced by way of the filling means.

This requires not only heating equipment for the substrate to be fermented but also at least one temperature sensor in the fermentation chamber, and an appropriate control circuit.

This type of temperature control is particularly effective because the temperature-controlled material introduced into the fermentation chamber immediately becomes distributed and rapidly passes its heat to the environment. Since no methane bacteria are yet present in the substrate to be fermented it can readily also be heated to a temperature which is above the ideal temperature of such bacteria. By virtue of the rapid dissipation of heat to the surrounding material, there is no adverse effect on the methane bacteria in the fermenter. Furthermore, because of good thermal conductivity and effective mixing, even a very slightly higher temperature of the substrate to be fermented is sufficient for effective temperature control of the fermenter, and again for this reason there need be no concern that the methane bacteria in the fermenter will be adversely affected. The overall effect is to permit faster and more uniform temperature control of the fermentation material, and this has advantages for the stability of the process.

It is preferable here that the filling means has been arranged between the two agitators. The temperature-controlled substrate to be fermented is thus introduced particularly effectively into the fermentation chamber and rapidly becomes mixed with the fermentation material, dissipating its heat particularly rapidly to the environment.

This also provides the possibility of pasteurizing or sterilizing the substrate to be fermented prior to introduction into the fermentation chamber. After introduction into the fermentation chamber, the substrate can thus be colonized particularly rapidly by methane bacteria, the result being that fermentation is promoted and therefore that yield is raised.

This type of temperature control moreover requires no presence of further heating equipment or heat exchangers in the fermentation chamber, and thus prevents the abovementioned adverse effects. This type of temperature control also requires no presence in the fermentation chamber of electrical circuits which could otherwise lead to a risk of sparking and thus of explosion.

In other preferred embodiments, there is equipment in the settling chamber to inhibit formation of surface scum at the overflow rim. This can, for example, be compressed-air equipment by way of which air or compressed biogas is injected from below into the settling chamber. The rising air bubbles cause disintegration of the surface scum and also cause active biomass to pass over the overflow rim and return to the fermentation chamber. The equipment mentioned can also be scraper equipment.

The gas store of the inventive fermenter is preferably composed of a film stretched over the open upper side of the fermentation chamber. This is in relatively slack suspension above the fermentation chamber until a large amount of gas has evolved, but then is displaced and stretched upward by the gas produced. The gas formed can then be removed in a known manner, using known removal apparatuses.

It is particularly preferable that the fermenter has a roof structure arranged over the gas store.

It is also preferable that there is no electrical equipment in the region of the fermentation chamber, of the gas store, and/or of the settling chamber. The fermentation chamber, the gas store, and/or the settling chamber can also have been designed as a Faraday cage. These two measures serve to prevent fire and explosion.

To this end, the housing of the fermenter can be composed entirely of a conductive metal (in particular V4A steel), or else of a non-metallic material to which a network composed of metallic conductors has been added, e.g. in the form of a wire mesh material surrounding the housing material.

In another preferred embodiment, the inventive fermenter has a sludge gutter arranged in the floor region of the fermentation chamber. Inorganic material, such as sand, lime, stones, etc., can settle in this gutter and can be removed from the fermenter for example with the aid of a screw conveyor. The usual daily amount of the fermentation material thus removed is from 1 to 3%. Solids can then be separated from the discharged material, and the liquid constituents can be returned to the fermentation chamber.

A process is also provided for producing biogas from organic material in a fermenter. This has the following steps:
a) introduction, via filling means, into a fermentation chamber with a essentially round base surface, of substrate to be fermented;
b) production of a circumferentially directed stream of material in the fermentation chamber by means of agitator equipment;
c) production and maintenance of an anaerobic environment, of a pH of at least 7, and of a temperature in the mesophilic to thermophilic range;
d) collection, in an unpressurized gas store, of the gas produced, and continuous or batchwise removal of the collected gas; and also
e) continuous or batchwise removal of fermentation material from the fermentation chamber and introduction into a settling chamber.

It is particularly preferable that the pH is in the range from pH 7 to pH 8 inclusive. The mesophilic temperature range mentioned encompasses temperatures from 30° C. to 45° C. inclusive. In contrast, the thermophilic temperature range mentioned encompasses temperatures from 42° C. to 60° C. inclusive. A particularly preferred temperature range is from 35° C. to 42° C. inclusive.

It is preferable here that the flow of material has, in addition to the circumferentially directed movement component, in a subregion, a movement component directed downward from the surface of the fermentation mass.

It is also preferable that in the settling chamber, active biomass rises and is returned to the fermentation chamber, whereas passive biomass sinks.

The expressions "active biomass" and "passive biomass" have been defined at an earlier stage above.

The passive biomass preferably passes into a fixed-bed reactor composed of porous solid material, where it continues to ferment, while residual exhausted fermentation material which has passed through the fixed-bed reactor is preferably removed continuously or batchwise and passed to storage.

It is particularly preferable that the removal of fermentation material from the fermentation chamber and its introduction into the settling chamber, and the removal of exhausted fermented residual material from the fixed-bed reactor take place in synchronized fashion. The volume of the fermentation material introduced into the settling chamber is preferably greater than the volume of the residual material removed from the fixed-bed reactor.

When the fermentation material is introduced into the settling chamber, the active biomass which has risen to the top in the chamber is thus displaced upward and discharged over the overflow rim, and can therefore be returned to the fermentation process in the fermentation chamber.

It is particularly preferable that the volume of the fermentation material introduced in the settling chamber is twice as great as the volume of the residual material removed from the fixed-bed reactor.

It is moreover preferable that formation of surface scum at the overflow rim is prevented via injection of compressed air or of compressed biogas into the settling chamber. As an alternative here, the formation of a scum layer at the overflow rim can be prevented via scraping with suitable equipment.

This procedure also prevents sediments or scum from adversely effecting, or interfering with, the function of the fixed-bed reactor.

The substrate to be fermented particularly preferably comprises components selected from the group consisting of animal excrement and animal feces, biological waste, renewable raw materials, and fermentable plants and plant parts.

The animal excrement and feces can, for example, be slurry, liquid waste, or dung. The biological wastes are, for example, residues from food production, potato distillation residues or potato skins, pressed oilseed cake, abattoir waste and/or food waste, spoiled fruit, vegetables, and food, animal litter, and edible fats and oils and the like. The renewable raw materials are, for example, maize silage, grass silage, wheat, cropped sugar beet, rapeseed, and the like. Fermen table plants and plant parts comprise, for example, grass cuttings, forage waste, straw, maize tops and beet tops.

Slurry is an anoxic system with relatively high pH and for this reason has very good suitability for creating the conditions required for methane bacteria in a biogas fermenter.

The invention is illustrated by way of example below with reference to the drawings. These show inventive examples which are not in any case intended to restrict the scope of protection of the claims submitted.

Figure 1:
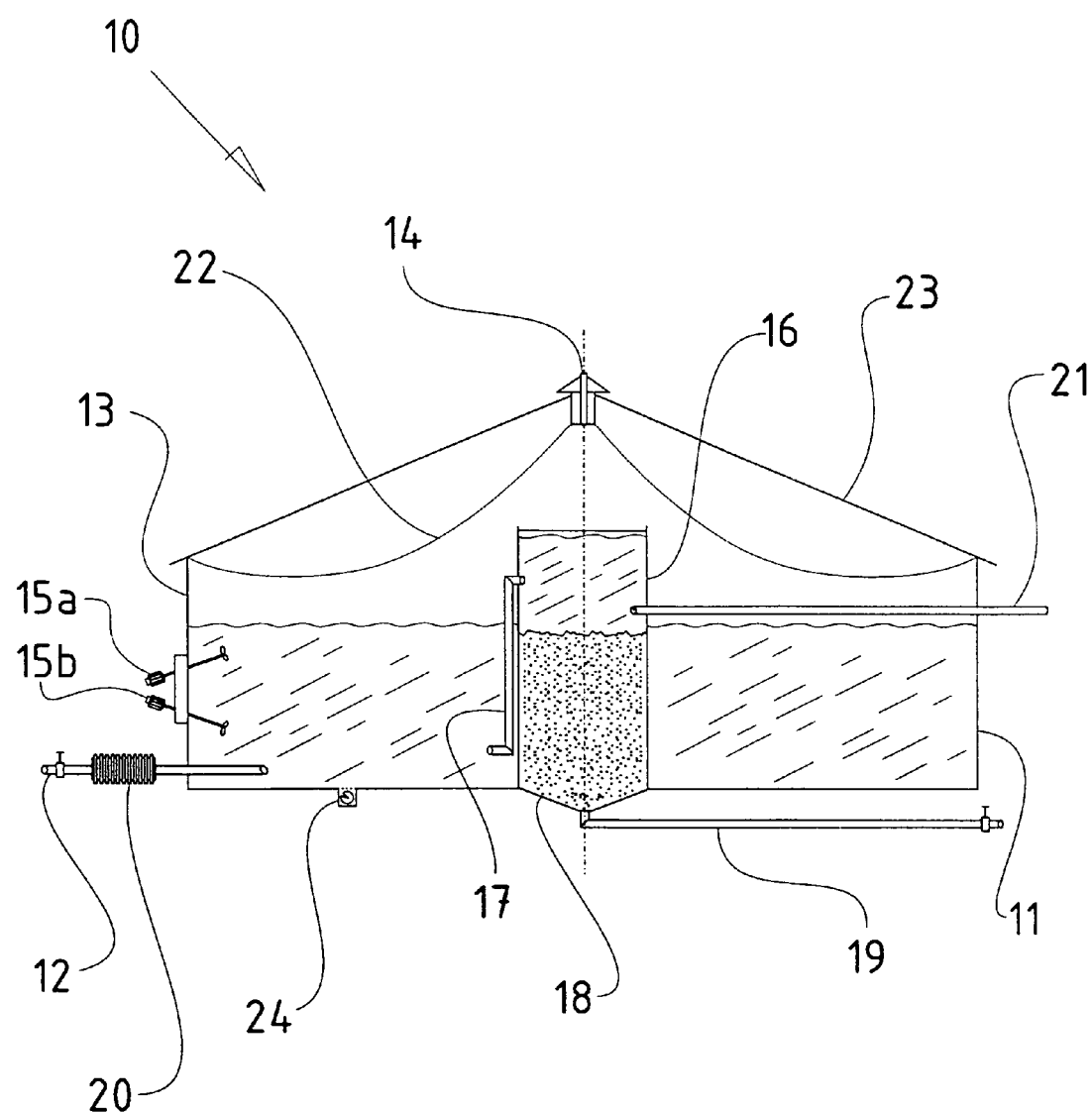
FIG. 1 shows: the cross section of an inventive fermenter for producing biogas from organic material.

FIG. 1 shows an inventive fermenter 10 for producing biogas from organic material. The fermenter has a fermentation chamber 11 with a essentially round base surface, this chamber being equipped to receive fermentation material (shown by oblique hatching). The fermenter also has, arranged in the peripheral region of the fermentation chamber, filling means 12 for substrate to be fermented, and also has, arranged above the fermentation chamber, an unpressurized gas store 13 with gas discharging means 14. Arranged in the peripheral region of the fermentation chamber, there is stirring means 15, composed of two agitators 15a, 15b, the direction of orientation of one of which is obliquely upward and of the other is obliquely downward. It is not discernible from FIG. 1 that the direction of orientation of each of the two agitators passes different sides of the central axis, shown by a broken line, of the fermentation chamber 10.

The fermenter also has a settling chamber 16 with an overflow rim, and pumping means 17 for the continuous or batchwise removal of fermentation material from the fermentation chamber and introduction into the settling chamber. The settling chamber 16 has been arranged in the middle of the fermentation chamber 11 which has an a essentially round base surface, and the fermentation chamber has therefore been designed in the form of an annular channel.

The settling chamber has, in its lower region, a fixed-bed reactor 18 composed of porous solid material, and also pumping means 19 for the removal of residual exhausted fermented material from the fixed-bed reactor. The fermentor also has, for the substrate to be fermented, temperature-control equipment 20, arranged in the region of the filling means 12. The fermenter also has compressed-air equipment 21 for the injection of compressed air into the settling chamber 16, and also has a roof structure 23, on which a film 22, which delimits the upper side of the gas store, has been suspended. The fermenter also has a sludge gutter 24 arranged in the bottom region of the fermentation chamber.

Figure 2:
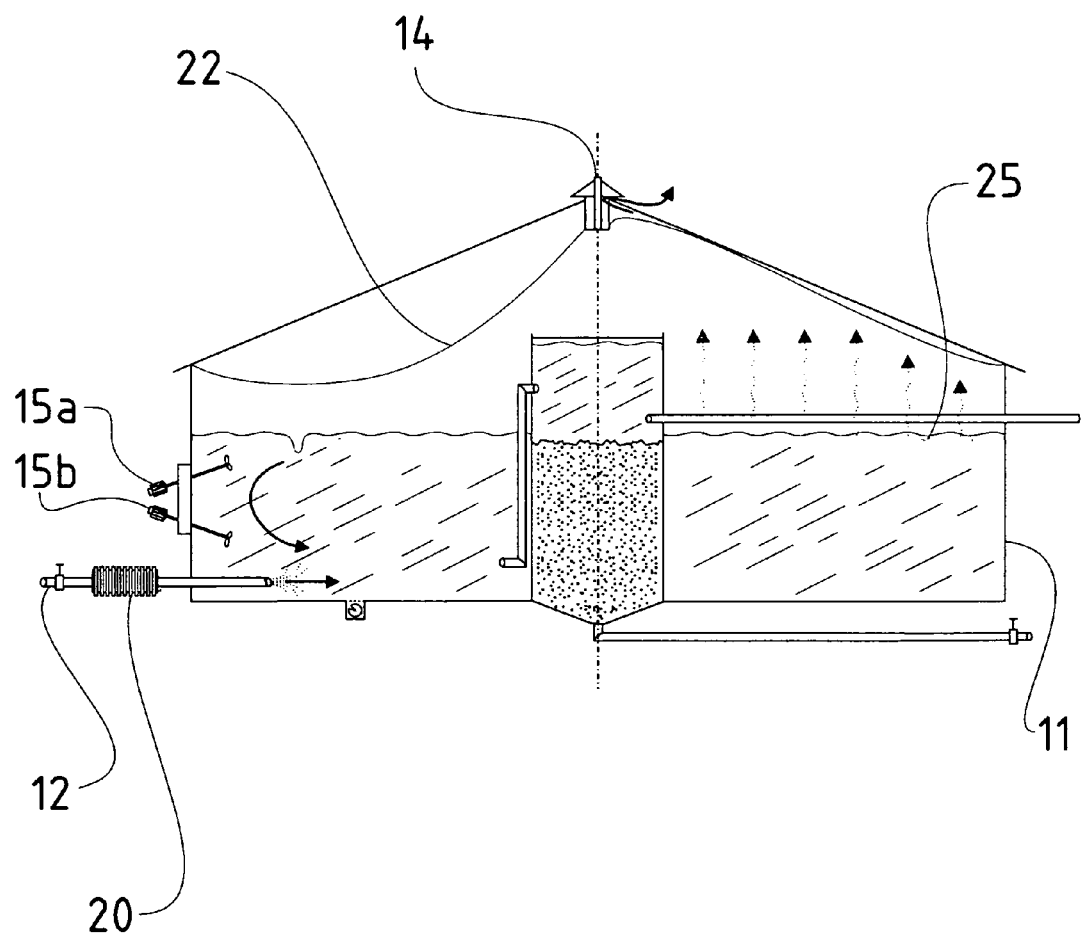
FIGS. 2 and 3 show: the functional principle of the inventive fermenter for producing biogas.

FIG. 2 shows various functional principles of the inventive fermenter. Substrate to be fermented, temperature-controlled in advance by means of the temperature-control equipment 20, is introduced into the fermentation chamber 11 via the filling means 12. The fermentation material located in the fermentation chamber is circulated by agitation with the aid of the stirring means 15, whereupon a circumferential flow of material becomes established. In that half of the fermenter that is shown on the right-hand side of the vertical axis it is discernible that the fermentation process has already started and biogas formed is escaping upward. In the right-hand half of the fermenter, the film 22, which is shown as still sagging in the left-hand half of the fermenter, has already been displaced upward and in turn is displacing air above it by way of a passage arranged in the region of the gas discharging means. FIG. 2 also shows a scum layer 25, which is composed of intermediates and of methanogenic substrates, which rise within the fermentation mass, because their density is relatively low. These substances become unavailable for metabolism by the microorganisms mentioned, in particular by the methane bacteria, and this reduces the yield of the fermenter. The left-hand half of the fermenter shown in FIG. 2 shows that the action of the stirring means 15 produces a flow of material directed downward which breaks up the scum layer and conveys the material located in the scum layer downward, where it is metabolized by the microorganisms mentioned.

Figure 3:
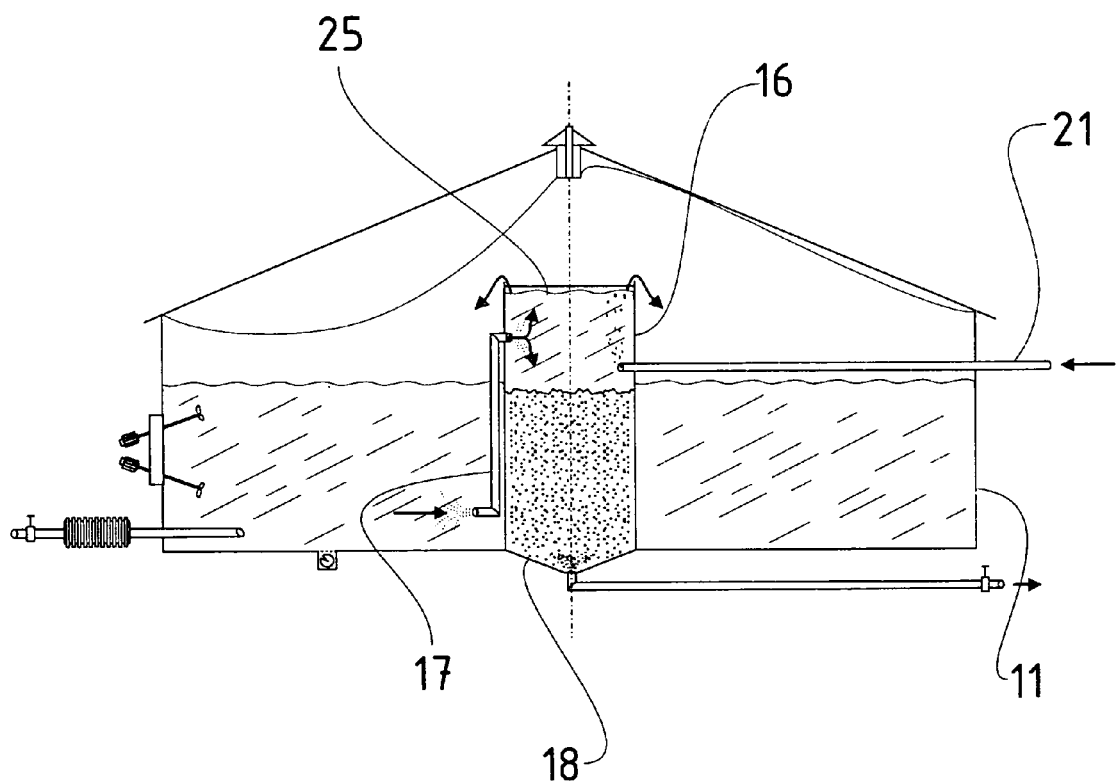

FIG. 3 shows that fermentation material is conveyed from the fermentation chamber 11 by way of the pumping means 17 into the settling chamber 16. The fermentation material is removed in the lower region of the fermentation chamber, in such a way that the content of active biomass has already been reduced, and it is introduced into the settling chamber 16 in a region situated below the overflow rim of the settling chamber 16, in such a way that when the fermentation material is introduced into the settling chamber, the scum layer 25 which has risen to the top in that chamber is displaced upward and runs over the overflow rim. The active biomass, which in particular comprises microorganisms, and also methanogenic substrates, can thus be reclaimed. This measure increases the yield, contributes to faster achievement of the ideal conditions in the fermenter, and moreover can give a higher OS load per unit of volume—with the above-mentioned advantages.

In contrast, substantially exhausted fermented material (passive biomass) sinks in the settling chamber 16 and passes into the fixed-bed reactor 18, which comprises a porous material, for example a bed composed of lava granules or of swellable clay particles. This material has a large internal surface area and with this provides many opportunities for colonization by microorganisms, and these provide for complete fermentation of the material.

Exhausted fermented material is removed from the fixed-bed reactor by way of the pumping means 19. The volume of the fermentation material introduced into the settling chamber here is preferably greater than the volume of the material removed from the fixed-bed reactor. When the fermentation material is introduced into the settling chamber, the active biomass which has risen to the top there is thus displaced upward and proceeds to run over the overflow rim, and can thus be reintroduced to the fermentation process in the fermentation chamber.

Compressed air is injected by way of the compressed-air line 21 continuously or batchwise into the settling chamber.

The rising air bubbles cause disintegration of the surface scum and also cause active biomass to pass over the overflow rim and to be returned to the fermentation chamber.

The conical design, not shown in FIG. 3, of the surface of the fixed-bed reactor can moreover give a further improvement in the discharge of the active biomass into the fermentation chamber.

Figure 4:
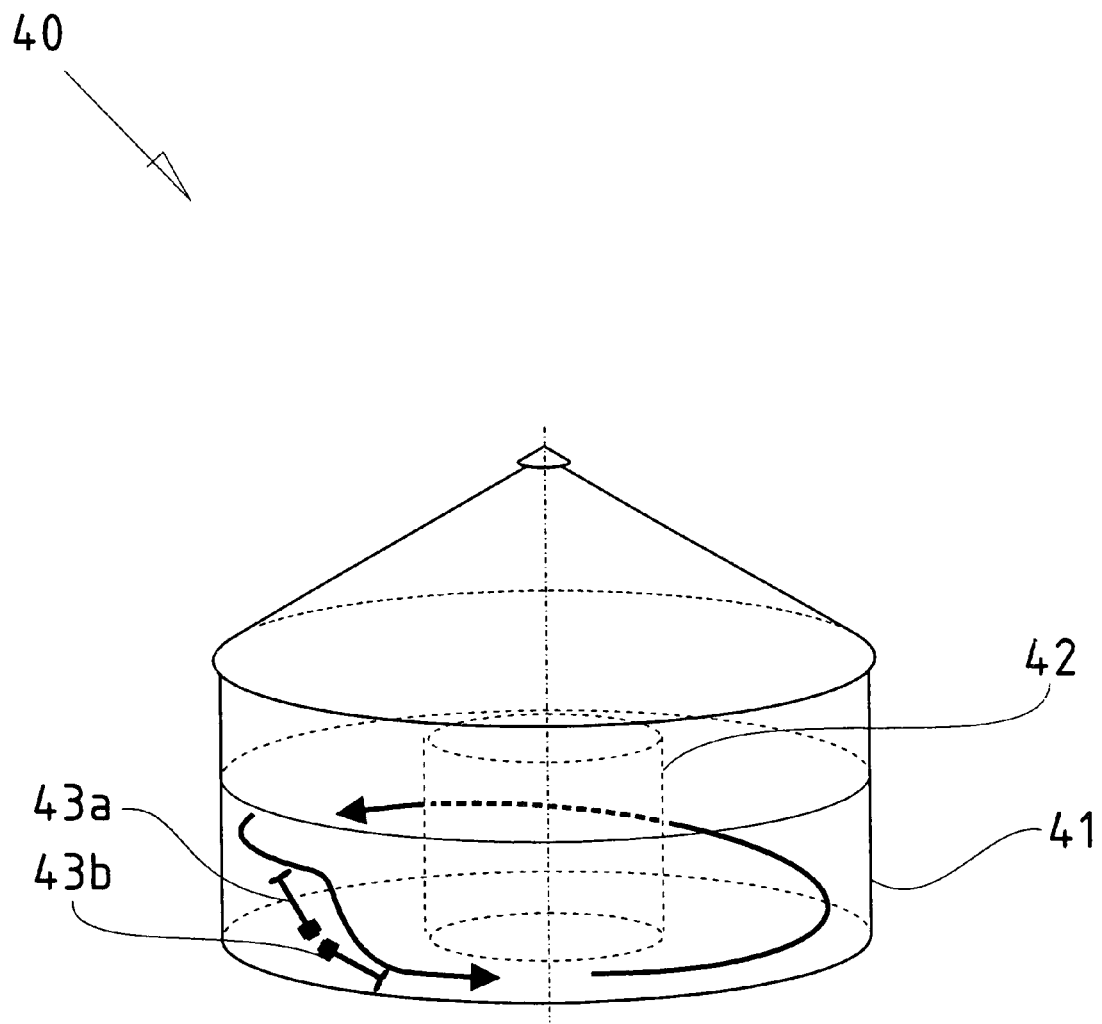
FIG. 4 shows: a perspective view of an inventive fermenter, showing how the flow of the fermentation material proceeds.

FIG. 4 shows a perspective view of an inventive fermenter 40 with a fermentation chamber 41, a settling chamber 42, and also agitator equipment 43. The agitator equipment is composed of two agitators 43a and 43b, the direction of orientation of one of which is obliquely upward, the direction of orientation of the other being obliquely downward, where the direction of orientation of each of the two agitators passes different sides of the vertical central axis of the fermentation chamber. This procedure can establish a flow of material which, in the region of the agitation equipment, is sigmoid, running downward, and which otherwise passes circumferentially through the fermentation chamber 41 designed in the form of an annular channel. This procedure firstly provides good mixing of the fermentation material and secondly prevents production of any scum layer, in such a way that the intermediates and methanogenic substrates are conveyed back into the fermentation mass and fed to the microorganisms. This measure increases yield, contributes to more rapid achievement of ideal conditions in the fermenter, and moreover permits higher OS loading per unit of volume—with the above-mentioned advantages.

What is claimed is:

1. A fermenter for producing biogas from organic fermentation material, having:
    a) a fermentation chamber with an essentially round base surface to receive the fermentation material for anaerobic processing;
    b) arranged, in a peripheral region of the fermentation chamber, filling means for the fermentation material to be fermented;
    c) arranged, above the fermentation chamber, an unpressurized gas store with gas discharging means;
    d) stirring means;
    e) a settling chamber with an overflow rim and, in its lower region, a fixed-bed reactor composed of porous solid material through which a volume of passive biomass must pass before being removed from the settling chamber; and
    f) pumping means for the continuous or batchwise removal of fermentation material from the fermentation chamber and the introduction thereof into the settling chamber in a region situated below the overflow rim, said pumping means being capable of introducing a volume of fermentation material into the settling chamber that is greater than the volume of passive biomass removed from the settling chamber such that active biomass can be displaced upward and run over the overflow rim to be returned to the fermentation chamber.

2. The fermenter as claimed in claim 1, wherein the fermentation chamber is in the form of an annular channel.

3. The fermenter as claimed in claim 1, wherein, below the fixed-bed reactor, there is a pumping means provided for the removal of exhausted fermented material.

4. The fermenter as claimed in claim 1, wherein the settling chamber is arranged in the center of the fermentation chamber.

5. The fermenter as claimed in claim 1, wherein the stirring means is arranged in the peripheral region of the fermentation chamber.

6. The fermenter as claimed in claim 1, wherein the stirring means sucks material from the surface of the fermentation mass and forces it obliquely downward so as to permit, in the region of the stirring means, production of a sigmoid flow of material, which otherwise passes circumferentially through the fermentation chamber.

7. The fermenter as claimed in claim 1, wherein the stirring means is composed of two agitators.

8. The fermenter as claimed in claim 1, wherein the stirring means is adjustable in relation to its angle with respect to the horizontal axis and/or with respect to the vertical axis.

9. The fermenter as claimed in claim 7, wherein the direction of orientation of one of the two agitators is obliquely upward and that of the other is obliquely downward, and the direction of orientation of each of the two agitators passes different sides of the vertical central axis of the fermentation chamber.

10. The fermenter as claimed in claim 1, wherein the fermenter further comprises temperature-control equipment set up such that the temperature of the fermentation material in the fermentation chamber can be adjusted solely via the temperature control of the fermentation material intended for fermentation and introduced by way of the filling means.

11. The fermenter as claimed in claim 7, wherein the filling means is arranged between the two agitators.

12. The fermenter as claimed in claim 1, wherein equipment for avoiding formation of surface scum is provided at the overflow rim in the settling chamber.

13. The fermenter as claimed in claim 12, wherein the equipment for avoiding formation of surface scum at the overflow rim is compressed-air equipment.

14. The fermenter as claimed in claim 1, wherein a film is stretched over an open upper side of the fermentation chamber to delimit an upper side of the gas store.

15. The fermenter as claimed in claim 1, wherein the fermenter has a roof structure arranged over the gas store.

16. The fermenter as claimed in claim 1, wherein there is no electric equipment provided in the region of the fermentation chamber, of the gas store, and/or of the settling chamber.

17. The fermenter as claimed in claim 1, wherein the fermentation chamber, the gas store, and/or the settling chamber comprises a Faraday cage.

18. The fermenter as claimed in claim 1, wherein the fermenter has a sludge gutter arranged in a floor region of the fermentation chamber.

19. A process for producing biogas from organic fermentation material using a fermenter according to claim 1, the method comprising:
   a) introducing, via filling means, the organic fermentation material into the fermentation chamber;
   b) producing a circumferentially directed stream of the organic fermentation material in the fermentation chamber by means of agitator equipment;
   c) producing and maintaining in the fermenter an anaerobic environment, of a pH of at least 7, and of a temperature in a mesophilic to thermophilic range;
   d) collecting, in an unpressurized gas store, biogas produced, and continuously or batchwise removing the collected biogas; and
   e) continuously or batchwise removing the organic fermentation material from the fermentation chamber and introducing the organic fermentation material into the settling chamber.

20. The process as claimed in claim 19, wherein the stream of organic fermentation material has, in addition to the circumferentially directed movement component, in a subregion, a movement component directed downward from the surface of the fermentation mass.

21. The process as claimed in claim 19, wherein, in the settling chamber, active biomass rises and is returned to the fermentation chamber, whereas passive biomass sinks.

22. The process as claimed in claim 21, wherein passive biomass passes into the fixed-bed reactor composed of porous solid material.

23. The process as claimed in claim 22, wherein exhausted fermented residual material which has passed through the fixed-bed reactor is removed and stored, continuously or batchwise.

24. The process as claimed in claim 22, wherein the removal of fermentation material from the fermentation chamber and its introduction into the settling chamber, and the removal of exhausted fermented residual material from the fixed-bed reactor take place in synchronized fashion.

25. The process as claimed in claim 22, wherein the volume of the fermentation material introduced into the settling chamber is greater than the volume of the residual material removed from the fixed-bed reactor.

26. The process as claimed in claim 19, wherein formation of surface scum at the overflow rim is prevented via injection of compressed air or of compressed biogas into the settling chamber.

27. The process as claimed in claim 19, wherein the organic fermentation material introduced into the fermenter to produce biogas comprises components selected from the group consisting of animal excrement and animal feces, biological waste, renewable raw materials, and fermentable plants and plant parts.

* * * * *